(12) United States Patent
Sugahara

(10) Patent No.: US 6,939,993 B2
(45) Date of Patent: Sep. 6, 2005

(54) METHOD FOR SEPARATION OF REACTION PRODUCTS FROM CATALYSTS

(75) Inventor: Michihiro Sugahara, Hyogo (JP)

(73) Assignee: Daicel Chemical Industries, Ltd., Osaka (JP)

(*) Notice: Subject to any disclaimer, the term of this patent is extended or adjusted under 35 U.S.C. 154(b) by 0 days.

(21) Appl. No.: 10/415,667

(22) PCT Filed: Oct. 25, 2001

(86) PCT No.: PCT/JP01/09407

§ 371 (c)(1),
(2), (4) Date: May 1, 2003

(87) PCT Pub. No.: WO02/36527

PCT Pub. Date: May 10, 2002

(65) Prior Publication Data

US 2004/0014985 A1 Jan. 22, 2004

(30) Foreign Application Priority Data

Nov. 1, 2000 (JP) ........................................ 2000-335177

(51) Int. Cl.$^7$ .................... C07C 45/00; C07C 43/11; C07C 27/26; C07D 209/04; C07D 207/40

(52) U.S. Cl. .................... 568/324; 568/340; 568/410; 568/621; 568/868; 548/545; 548/469; 548/473

(58) Field of Search ................ 568/324, 340, 568/410, 621, 868; 548/545, 469, 473

(56) References Cited

U.S. PATENT DOCUMENTS 5,030,739 A * 7/1991 Foricher et al. ............. 552/542
6,133,488 A * 10/2000 Hirai ........................... 568/818

FOREIGN PATENT DOCUMENTS

| EP | 0 825 165 A2 | 2/1998 |
|---|---|---|
| JP | 8-38909 | 8/1994 |
| JP | 9-278675 | 7/1996 |
| JP | 10-114702 | 8/1996 |
| JP | 9-327626 | 2/1997 |
| JP | 10-316610 | 5/1997 |
| JP | 11-239730 | 1/1998 |
| JP | 99/41219 | 2/1999 |
| JP | 99/50204 | 3/1999 |
| JP | 2001-288122 A | 10/2001 |

* cited by examiner

*Primary Examiner*—Johann Richter
*Assistant Examiner*—Sikarl A. Witherspoon
(74) *Attorney, Agent, or Firm*—Birch, Stewart, Kolasch & Birch, LLP

(57) ABSTRACT

Method for separating reaction product from imide compound catalyst represented by Formula (1) or derivative thereof in reaction mixture obtained by reaction in presence of imide compound catalyst:

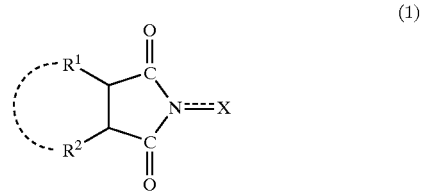

(1)

wherein $R^1$ and $R^2$ are each, for example, a hydrogen atom or an alkyl group, where $R^1$ and $R^2$ may be combined to form a double bond, an aromatic ring, or a non-aromatic ring, and X is an oxygen atom or a hydroxyl group. The method includes an extraction process using two organic solvents separable from each other to thereby separate the reaction product into one organic solvent layer and the imide compound catalyst component into the other organic solvent layer. The disclosed method efficiently and simply separates the reaction product from the catalyst component.

7 Claims, No Drawings

METHOD FOR SEPARATION OF REACTION PRODUCTS FROM CATALYSTS this application is the national phase under 35 U.S.C. § 371 of PCT International Application No. PCT/JP01/09407 which has an International filing date of Oct. 25, 2001, which designated the United States of America.

TECHNICAL FIELD

The present invention relates to a method for separating a reaction product from an imide compound catalyst such as N-hydroxyphthalimide and/or an altered derivative thereof in a reaction mixture obtained as a result of a reaction using the imide compound catalyst.

BACKGROUND ART

Catalytic imide compounds such as N-hydroxyphthalimide receive attention as catalysts that can allow various reactions to proceed smoothly under mild conditions. Such reactions include, for example, oxidation with molecular oxygen, carboxylation, nitration, sulfonation, acylation, and radical coupling reactions.

For example, Japanese Unexamined Patent Application Publications No. 08-38909 and No. 09-327626 each disclose a process for oxidizing a substrate, such as a hydrocarbon or an alcohol, with molecular oxygen in the presence of an imide compound catalyst to thereby yield, for example, a corresponding alcohol, aldehyde, ketone, and/or carboxylic acid. Japanese Unexamined Patent Application Publication No. 09-278675 discloses an oxidation process of a conjugated compound using the imide compound catalyst. Japanese Unexamined Patent Application Publication No. 10-316610 describes that esters, acid anhydrides, lactones or other products are formed by oxidizing ethers in the presence of the imide compound catalyst. PCT International Publication No. WO 99/50204 discloses a process for producing a corresponding epoxide by oxidizing a compound having a non-aromatic ethylene bond with molecular oxygen in the presence of the imide compound catalyst and a co-oxidizing agent, and a process for producing a corresponding ester or lactone by oxidizing a ketone with molecular oxygen in the presence of the imide compound catalyst and the co-oxidizing agent.

Japanese Unexamined Patent Application Publication No. 11-239730 discloses a process for producing a corresponding nitro compound by allowing a substrate to react with a nitrogen oxide in the presence of an imide compound catalyst, and a process for producing a corresponding carboxylic acid by allowing a substrate to react with carbon monoxide and oxygen in the presence of the catalyst. PCT International Publication No. WO 99/41219 mentions that an acylation reaction of a substrate with oxygen and a 1,2-dicarbonyl compound such as biacetyl in the presence of the imide compound catalyst can proceed under mild conditions. The Chemical Society of Japan, Spring Annual Meeting, Lecture Proceedings (1999) reports that a radical coupling reaction of an α, β-unsaturated ester with an alcohol and oxygen proceeds by catalysis of N-hydroxyphthalimide and thereby yields an α-hydroxy-γ-butyrolactone in a good yield. The Lecture Proceedings also reports that a reaction of a hydrocarbon such as adamantane with oxygen and sulfur dioxide by catalysis of N-hydroxyphthalimide yields a corresponding sulfonic acid.

As is described above, the imide compound catalysts are very useful as catalysts for wide variety of organic synthesis reactions such as oxidation reactions. However, few reports have been made on a method for separating a reaction product from the imide compound catalyst after the completion of the reaction. For example, Japanese Unexamined Patent Application Publication No. 10-114702 discloses a method for separating a reaction product from an imide compound catalyst in an oxidation reaction mixture obtained as a result of a reaction using the imide compound catalyst. The method includes the steps of using an aqueous solvent containing at least water and a water-insoluble solvent separable from the aqueous solvent and dividing the oxidation reaction product into the aqueous solvent layer and the oxidizing catalyst into the water-insoluble solvent layer. However, this method cannot significantly separate a water-insoluble reaction product from a water-insoluble or water-soluble catalyst, although it can be an effective means for separating a water-soluble oxidation reaction product from a water-insoluble catalyst.

The imide compound catalyst may be partially altered after a reaction under some conditions. If a decomposed product or another altered derivative of the catalyst contaminates an end product of the reaction product, it may deteriorate the quality of the end product. However, no separation method for such altered derivatives has been known.

DISCLOSURE OF INVENTION

Accordingly, an object of the present invention to provide a method for efficiently and simply separating a reaction product from N-hydroxyphthalimide or another imide compound catalyst and/or an altered derivative of the catalyst in a reaction mixture obtained as a result of a reaction of a hydrocarbon or another substrate using the imide compound catalyst.

After intensive investigations to achieve the above object, the present inventors have found that a reaction product can be efficiently separated from an imide compound catalyst such as N-hydroxyphthalimide and/or an altered derivative of the catalyst in a reaction mixture obtained as a result of a reaction using the imide compound catalyst, by using two organic solvents separable from each other as extraction solvents and allowing the reaction product to pass into one organic solvent layer and the imide compound catalyst and/or an altered derivative thereof (hereinafter may be referred to as "altered catalyst") to pass into the other organic solvent layer. The present invention has been accomplished based on these findings.

Specifically, the present invention provides a method for separating a reaction product from an imide compound catalyst represented by Formula (1) or an altered derivative thereof in a reaction mixture obtained as a result of a reaction in the presence of the imide compound catalyst, the method including the step of performing an extraction process using two organic solvents separable from each other to thereby separate the reaction product into one organic solvent layer and the imide compound catalyst and/or an altered derivative thereof into the other organic solvent layer, respectively:

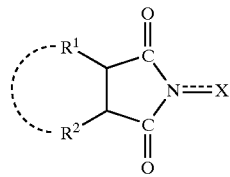

(1)

wherein $R^1$ and $R^2$ are the same or different and are each a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, an aromatic ring, or a non-aromatic ring; X is an oxygen atom or a hydroxyl group; and one or two of an N-substituted cyclic imido group indicated in the formula may be further formed on the $R^1$, $R^2$, or on the double bond, aromatic ring, or non-aromatic ring formed by $R^1$ and $R^2$.

The imide compound includes, for example, N-hydroxyphthalimide and other N-hydroxyimide compounds. The reaction product includes, for example, alcohols, aldehydes, ketones, carboxylic acids, epoxy compounds, esters, acid anhydrides, lactones, acetals, ethers, sulfides, amides, lactams, Schiff bases, oximes, nitro compounds, organic sulfur acids, and hydrocarbons. Preferred reaction products include, for example, terpenes (chain terpenes and cyclic terpenes) each having a carbonyl group.

One of the two organic solvents can be a solvent selected from aliphatic hydrocarbons and alicyclic hydrocarbons, and the other can be a solvent selected from nitrites, alcohols, ketones, acid anhydrides, carboxylic acids, amides, amines, nitrogen-containing heterocyclic compounds, ethers, sulfoxides, sulfones, and nitroalkanes.

The organic solvent layer containing the reaction product after the extraction process (extraction operation) may be further subjected to washing with water. The term "imide compound catalyst or an altered derivative thereof" as used in the present invention means at least one of the imide compound catalyst and an altered derivative thereof and includes the case of both the imide compound catalyst and an altered derivative thereof.

BEST MODE FOR CARRYING OUT THE INVENTION

[Imide Compounds]

Of the substituents $R^1$ and $R^2$ in the imide compounds represented by Formula (1), the halogen atom includes iodine, bromine, chlorine, and fluorine atoms. The alkyl group includes, but is not limited to, methyl, ethyl, propyl, isopropyl, butyl, isobutyl, s-butyl, t-butyl, pentyl, hexyl, heptyl, octyl, decyl, and other straight- or branched-chain alkyl groups each containing from about 1 to about 10 carbon atoms. Preferred alkyl groups are alkyl groups each containing from about 1 to about 6 carbon atoms, of which lower alkyl groups each containing from about 1 to about 4 carbon atoms are typically preferred.

The aryl group includes phenyl and naphthyl groups, for example. Examples of the cycloalkyl group include cyclopentyl, cyclohexyl, and cyclooctyl groups. Examples of the alkoxy group are methoxy, ethoxy, propoxy, isopropoxy, butoxy, isobutoxy, t-butoxy, pentyloxy, hexyloxy, and other alkoxy groups each containing from about 1 to about 10 carbon atoms, and preferably containing from about 1 to about 6 carbon atoms. Among them, lower alkoxy groups each containing from about 1 to about 4 carbon atoms are typically preferred.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each containing from about 1 to about 10 carbon atoms in their alkoxy moiety. Preferred alkoxycarbonyl groups are alkoxycarbonyl groups each containing from about 1 to about 6 carbon atoms in their alkoxy moiety, of which lower alkoxycarbonyl groups each containing from about 1 to about 4 carbon atoms in their alkoxy moiety are typically preferred.

The acyl group includes, but is not limited to, formyl, acetyl, propionyl, butyryl, isobutyryl, valeryl, isovaleryl, pivaloyl, and other acyl groups each containing from about 1 to about 6 carbon atoms.

The substituents $R^1$ and $R^2$ may be identical to or different from each other. The substituents $R^1$ and $R^2$ in Formula (1) may be combined to form a double bond, an aromatic ring, or a non-aromatic ring. The preferred aromatic or non-aromatic ring is a 5- to 12-membered ring, of which a 6- to 10-membered ring is typically preferred. The ring may be a heterocyclic ring or condensed heterocyclic ring, but it is often a hydrocarbon ring. Such rings include, but are not limited to, non-aromatic alicyclic rings such as cyclohexane ring and other cycloalkane rings which may have a substituent, cyclohexene ring and other cycloalkene rings which may have a substituent; non-aromatic bridged rings such as 5-norbornene ring and other bridged hydrocarbon rings which may have a substituent; benzene ring, naphthalene ring, and other aromatic rings (including condensed rings) which may have a substituent. The ring often comprises an aromatic ring. The ring may have at least one substituent. Such substituents include, for example, alkyl groups, haloalkyl groups, hydroxyl group, alkoxy groups, carboxyl group, alkoxycarbonyl groups, acyl groups, nitro group, cyano group, amino groups, and halogen atoms.

In Formula (1), X represents an oxygen atom or a hydroxyl group, and the bond between the nitrogen atom N and X is a single bond or a double bond.

On $R^1$, $R^2$, or on the double bond or aromatic or non-aromatic ring formed by $R^1$ and $R^2$, one or two of the N-substituted cyclic imido group indicated in Formula (1) may be further formed. For example, when $R^1$ or $R^2$ is an alkyl group containing two or more carbon atoms, the N-substituted cyclic imido group may be formed together with the adjacent two carbon atoms constituting the alkyl group. Likewise, when $R^1$ and $R^2$ are combined to form a double bond, the N-substituted cyclic imido group may be formed together with the double bond. When $R^1$ and $R^2$ are combined to form an aromatic or non-aromatic ring, the N-substituted cyclic imido group may be formed with the adjacent two carbon atoms constituting the ring. Each of these imide compounds represented by Formula (1) can be used alone or in combination in a reaction.

Preferred imide compounds include compounds of the following formulae:

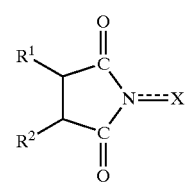

(1a)

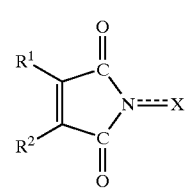

(1b)

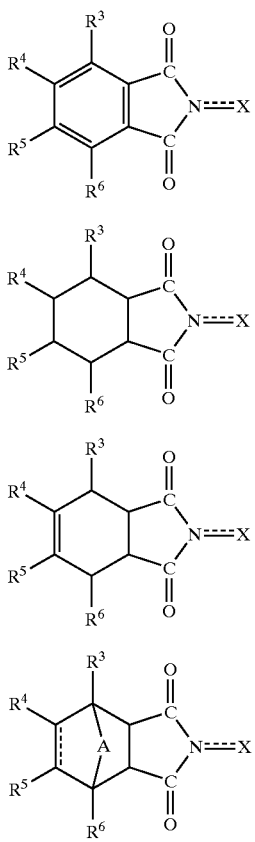

wherein $R^3$ to $R^6$ are the same or different and are each a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom, where adjacent groups of $R^3$ to $R^6$ may be combined to form an aromatic or non-aromatic ring; A in Formula (1f) is a methylene group or an oxygen atom; and $R^1$, $R^2$ and X have the same meanings as defined above, and wherein one or two of an N-substituted cyclic imido group indicated in Formula (1c) may be further formed on a benzene ring in Formula (1c)

In the substituents $R^3$ to $R^6$, the alkyl group includes similar alkyl groups to those exemplified above, of which alkyl groups each containing from about 1 to about 6 carbon atoms are preferred. The haloalkyl group includes trifluoromethyl group and other haloalkyl groups each containing from about 1 to about 4 carbon atoms. The alkoxy group includes similar alkoxy groups to those mentioned above, of which lower alkoxy groups each containing from about 1 to about 4 carbon atoms are preferred. The alkoxycarbonyl group includes similar alkoxycarbonyl groups to those described above, of which lower alkoxycarbonyl groups each containing from about 1 to about 4 carbon atoms in the alkoxy moiety are preferred. The acyl group includes similar acyl groups to those described above, of which acyl groups each containing from about 1 to about 6 carbon atoms are preferred. The illustrative halogen atoms include fluorine, chlorine and bromine atoms. Each of the substituents $R^3$ to $R^6$ is often a hydrogen atom, a lower alkyl group having from about 1 to about 4 carbon atoms, a carboxyl group, a nitro group, or a halogen atom. The ring formed together by $R^3$ to $R^6$ includes similar rings to the aforementioned rings which are formed by $R^1$ and $R^2$. Among them, aromatic or non-aromatic 5- to 12-membered rings are typically preferred.

The imide compounds represented by Formula (1) can be prepared by a conventional imidization process (a process for the formation of an imide), such as a process in which a corresponding acid anhydride is allowed to react with hydroxylamine $NH_2OH$ for ring-opening of an acid anhydride group, and the ring is then closed to form an imide.

Such acid anhydrides include, for example, succinic anhydride, maleic anhydride, and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-dianhydride, and other saturated or unsaturated non-aromatic cyclic polycarboxylic anhydrides (alicyclic polycarboxylic anhydrides), HET anhydride (chlorendic anhydride), himic anhydride, and other bridged polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

Preferred imide compounds include, for example, imide compounds derived from aliphatic polycarboxylic anhydrides, such as N-hydroxysuccinimide and N-hydroxymaleimide; and imide compounds derived from alicyclic polycarboxylic anhydrides or aromatic polycarboxylic anhydrides, such as N-hydroxyhexahydrophthalimide, N, N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

[Promoters (Co-catalysts)]

The imide compound can be used in combination with a promoter (co-catalyst). Such promoters include, but are not limited to, compounds each containing a transition metal or a Group 13 element of the Periodic Table of Elements. Such compounds include, but are not limited to, oxides, hydrides, nitrides, oxoacids or salts thereof, oxoacid esters, heteropolyacids or salts thereof, organic acid salts, inorganic acid salts, halides, and complexes. Each of these promoters can be used alone or in combination.

Elements of the transition metals include, for example, Group 3 elements (e.g., scandium Sc, yttrium Y; as well as cerium Ce, samarium Sm, and other lanthanoid elements; and actinium Ac and other actinoid elements), Group 4 elements (e.g., titanium Ti and zirconium Zr), Group 5 elements (e.g., vanadium V and niobium Nb), Group 6 elements (e.g., chromium Cr, molybdenum Mo, and tungsten W), Group 7 elements (e.g., manganese Mn, technetium Tc, and rhenium Re), Group 8 elements (e.g., iron Fe and ruthenium Ru), Group 9 elements (e.g., cobalt Co and rhodium Rh), Group 10 elements (e.g., nickel Ni, palladium Pd, and platinum Pt), and Group 11 elements (e.g., copper Cu), of the Periodic Table of Elements. Preferred elements include Ce, V, Nb, Cr, Mo, W, Mn, Fe, Ru, Co, Rh, Ni, and Cu. Group 13 elements of the Periodic Table of Elements include, for example, boron B and aluminium Al.

[Substrates and Reaction Products]

Compounds for use as a raw material (substrate) in the reaction include a variety of compounds each having a moiety or site that allows oxidation with molecular oxygen, carboxylation, nitration, sulfonation, acylation, radical coupling, and other reactions (refer to the literatures described in "Background Art"). Each of these compounds can be used alone or in combination.

Typical examples of the substrates are hydrocarbons, alcohols, aldehydes, ketones, amines, heterocyclic compounds, thiols, sulfides, and amides. Among them, hydrocarbons, alcohols aldehydes, and ketones are preferred as the substrates.

The hydrocarbons include, for example, saturated or unsaturated aliphatic hydrocarbons which may have a substituent, saturated or unsaturated alicyclic hydrocarbons which may have a substituent, completely or partially hydrogenated condensed polycyclic hydrocarbons and other condensed cyclic hydrocarbons each containing a non-aromatic ring, bridged hydrocarbons each containing a tertiary carbon atom (a methine carbon), and aromatic hydrocarbons each having a methyl group or methylene group combined with their aromatic ring.

Examples of the saturated or unsaturated aliphatic hydrocarbons are butane, isobutane, pentane, hexane, octane, decane, and other $C_4$–$C_{20}$ saturated hydrocarbons, of which branched saturated hydrocarbons are preferred; 1-butene, 2-butene, isobutene, 1-hexene, 1-octene, and other $C_4$–$C_{20}$ olefinic hydrocarbons; butadiene (1,3-butadiene), isoprene (2-methyl-1,3-butadiene), and other conjugated dienes; geraniol, geraniol esters, citronellol, citronellol esters, nerol, nerol esters, linalool, linalool esters, citral, citronellal, dihydromyrcene, and other chain terpenes.

The saturated or unsaturated alicyclic hydrocarbons include, but are not limited to, cycloalkanes such as cyclobutane, cyclopentane, cyclohexane, cycloheptane, cyclooctane, cyclononane, cyclodecane, cycloundecane, cyclododecane, cyclotridecane, cyclotetradecane, cyclooctadecane, cycloicosane, cyclodocosane, and cyclotetracosane, cyclotriacontane; cyclic olefins such as cyclopropene, cyclobutene, cyclopentene, cyclohexene, cycloheptene, cyclooctene, cyclononene, and cyclodecene; cycloalkadienes such as cyclopentadiene, 1,3-cyclohexadiene, 1,4-cyclohexadiene, 1,3-cycloheptadiene and other cycloheptadienes, 1,5-cyclooctadiene and other cyclooctadienes; cycloalkatrienes such as cyclooctatrienes; cycloalkatetraenes such as cyclooctatetraene; monocyclic terpenes such as limonene, α-terpinene, β-terpinene, γ-terpinene, terpinolene, 1-p-menthene, 3-p-menthene, cis-carveol, and trans-carveol. Preferred alicyclic hydrocarbons are alicyclic hydrocarbons each containing a ring having from about 3 to about 30 members, preferably a ring having from about 3 to about 25 members, typically a ring having from about 3 to about 20 members, especially a ring having from about 5 to about 20 members, and often a ring having from about 5 to about 16 members.

The condensed polycyclic hydrocarbons, bridged hydrocarbons, and other polycyclic hydrocarbons include compounds each having at least one methylidine group (i.e., a methine carbon-hydrogen bond —CH<) at a bridgehead position and/or a junction position (a junction position between rings) The completely or partially hydrogenated condensed polycyclic hydrocarbons and other condensed polycyclic hydrocarbons each containing a non-aromatic ring include, but are not limited to, acenaphthene, fluorene, tetralin, indene, indan, perhydroanthracene, perhydrophenanthrene, perhydrophenalene, perhydroacenaphthylene, decalin, and hexahydroindan. These often have a 5- to 8-membered ring (specifically a 5- or 6-membered ring) condensed therewith.

The bridged hydrocarbons include, but are not limited to, bicyclic hydrocarbons such as pinane, pinene, bornane, norbornane, norbornene, bicyclo[3.2.1] octane, and [4.3.2] undecane; tricyclic hydrocarbons such as adamantane, exotricyclo[5.2.1.0$^{2,6}$]decane, and endotricyclo[5.2.1.0$^{2,6}$] decane; tetracyclic hydrocarbons such as tetracyclo [4.4.0.1$^{2,5}$0.1$^{7,10}$]dodecane; as well as dicyclohexadiene, dicyclopentadiene, and other dimers of dienes, hydrogenated products of these dimers, such as dicyclohexane and dicyclopentane, and derivatives of these compounds; terpenes such as bicyclic monoterpenes, bicyclic sesquiterpenes, tricyclic sesquiterpenes, diterpenes, triterpenes, tetraterpenes, polyterpenes, and derivatives of these compounds; and steroids such as cholesterol and cholesterol esters. Examples of the terpenes include α-pinene, α-cedrene, valencene, isolongifolene, cadinene, selinene, caryophyllenes, and β-thujopsene. As the bridged hydrocarbons, pinane, bornane, norbornane, norbornene, adamantane, terpenes, steroids, and other bicyclic, tricyclic, and tetracyclic hydrocarbons each containing about 6 to about 16 carbon atoms, preferably about 6 to about 14 carbon atoms in their ring are often used.

The aromatic hydrocarbons each having a methyl group or methylene group combined with their aromatic ring may be any compounds each having at least one methyl group or methylene group substituted on an aromatic ring, and the aromatic ring may be any of aromatic hydrocarbon rings and aromatic heterocyclic rings. Such compound include, but are not limited to, toluene, o-, m- and p-xylenes, 1,2,3-trimethylbenzene, mesitylene, 1,2,3,4-tetramethylbenzene, durene, 4-t-butyl-1-methylbenzene, ethylbenzene, propylbenzene, cumene, o-, m- and p-ethyltoluenes, 1-methylnaphthalene, 2-methylnaphthalene, 1,5-dimethylnaphthalene, 2,5-dimethylnaphthalene, 1-methylanthracene, 2-methylanthracene, 9-methylanthracene, 4,4'-dimethylbiphenyl, dibenzyl, diphenylmethane, and triphenylmethane. Among them, $C_6$–$C_{10}$ aromatic hydrocarbons each containing about one to about four substituted methyl groups per molecule are typically preferred.

The hydrocarbons may have at least one substituent according to their types. Such substituents include, but are not limited to, halogen atoms, alkyl groups, alkenyl groups, aryl groups, heterocyclic groups, oxo group, hydroxyl group, alkoxy groups, hydroxyalkyl groups, carboxyl group, alkoxycarbonyl group, acyl groups, amino group, substituted amino groups, cyano group, and nitro group.

Preferred hydrocarbons include (1) conjugated dienes such as butadiene and isoprene, (2) compounds each having a carbon-hydrogen bond at the adjacent position to an unsaturated bond, such as 2-butene and other $C_4$–$C_{20}$ olefinic hydrocarbons, and chain terpenes, (3) alicyclic hydrocarbons such as cyclohexane, methylcyclohexane, and other cycloalkanes each having a 5- to 16-membered ring; cyclohexene and other cycloalkenes each having a 5- to 16-membered ring; cyclic terpenes; and steroids, (4) condensed cyclic compounds each having a non-aromatic ring (e.g., a cycloalkane ring or heterocyclic ring), such as decalin, tetralin, and fluorene, (5) bridged hydrocarbons containing a tertiary carbon atom (a methine carbon), such as adamantane and norbornene, (6) aromatic hydrocarbons each having a methyl group or methylene group combined with an aromatic ring, such as toluene, o-, m- and p-xylenes, p-t-butyltoluene, and other $C_6$–$C_{10}$ aromatic hydrocarbons each having one to four methyl groups, and diphenyl methane and other aromatic hydrocarbons each having a methylene group combined with an aromatic ring.

Oxidation of the hydrocarbons by oxygen in the presence of the imide compound catalyst yields corresponding oxides such as alcohols, aldehydes, ketones, carboxylic acids, epoxy compounds, lactones, acid anhydrides, acetals, and esters. For example, oxidation of conjugated dienes yields corresponding alkenediols. For example, oxidation of butadiene yields butenediols such as cis-isomer or trans-isomer of 2-butene-1,4-diol or 1-butene-3,4-diol. The positions of hydroxyl groups herein are not specifically limited. In oxidation of a compound having a carbon-hydrogen bond at the adjacent position to an unsaturated bond, the adjacent position to the unsaturated bond is oxidized. Oxidation of an alicyclic hydrocarbon introduces a hydroxyl group or oxo group into its ring, and under some conditions, the ring is further oxidatively cleaved to thereby yield, for example, a dicarboxylic acid. Oxidation of a condensed cyclic compound containing a non-aromatic ring introduces a hydroxyl group or oxo group into the non-aromatic ring, and under some conditions, the ring is further cleaved to thereby yield, for example, a dicarboxylic acid. Oxidation of a bridged hydrocarbon containing a tertiary carbon atom (a methine carbon) introduces a hydroxyl group into the tertiary carbon atom (e.g., at a bridgehead position), or, under some reaction conditions, introduces an oxo group into the adjacent position to the tertiary carbon atom. Oxidation of an aromatic hydrocarbon having a methyl group or methylene group combined with an aromatic ring permits the methyl group or methylene group to be oxidized to thereby yield a corresponding alcohol, aldehyde, ketone or carboxylic acid depending on conditions.

Specifically, by oxidizing an unsaturated compound having a methylene group (inclusive of a methyl group) at the adjacent position to a carbon-carbon double bond, a corresponding conjugated unsaturated carbonyl compound having an oxo group introduced into a carbon atom of the methylene group is formed. Such unsaturated compounds include, for example, $C_4$–$C_{20}$ olefinic hydrocarbons, chain terpenes, and other chain unsaturated compounds; cycloalkenes, cyclic terpenes, steroids, and other monocyclic or polycyclic unsaturated compounds each having a carbon-carbon double bond on their ring. More specifically, oxidation of valencene (2) by oxygen in the presence of the imide compound catalyst yields nootkatone (3) as shown in the following formula.

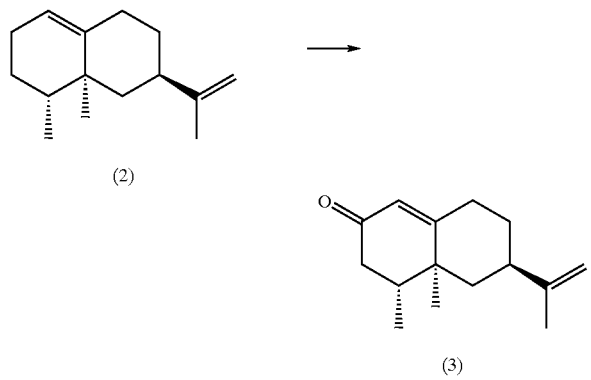

Reactions of the hydrocarbons with oxygen and carbon monoxide, nitrogen oxides (e.g., NO, $NO_2$, $N_2O_3$), sulfur oxides (e.g., $SO_2$), 1,2-dicarbonyl compounds, or compounds that can undergo a radical carbon-carbon bond formation reaction in the presence of the imide compound catalyst yield corresponding carboxylic acids, nitro compounds, organic sulfur acids (e.g., sulfonic acid), acylation reaction products (aldehydes, and ketones), or products of the carbon-carbon bond formation reaction or derivatives thereof (e.g., oxides, lactones and other cyclized products), respectively. For example, the reactions of bridged hydrocarbons each containing a tertiary carbon atom (a methine carbon) with oxygen and carbon monoxide, nitrogen oxides (e.g., NO, $NO_2$, $N_2O_3$), sulfur oxides (e.g., $SO_2$), 1,2-dicarbonyl compounds, or compounds that can undergo a radical carbon-carbon bond formation reaction in the presence of the imide compound catalyst yield compounds each having, for example, a carboxyl group, nitro group, sulfo group, acyl group or hydrocarbon group introduced into the tertiary carbon atom, or derivatives thereof.

The alcohols as the substrates include alcohol derivatives of the hydrocarbons, such as aliphatic monohydric alcohols, aliphatic polyhydric alcohols, alicyclic monohydric alcohols, alicyclic polyhydric alcohols, and aromatic alcohols.

The aliphatic monohydric alcohols include, but are not limited to, methanol, ethanol, 1-propanol, isopropanol, 1-butanol, isobutanol, 1-pentanol, 2-pentanol, neopentyl alcohol, 1-hexanol, 1-octanol, 1-decanol, 1-dodecanol, myristyl alcohol, 1-hexadecanol, and other $C_1$–$C_{20}$ saturated aliphatic alcohols; allyl alcohol, crotyl alcohol, propargyl alcohol, citronellol, geraniol, and other unsaturated aliphatic alcohols. The aliphatic polyhydric alcohols include, but are not limited to, ethylene glycol, propylene glycol, trimethylene glycol, 1,2-butanediol, 1,3-butanediol, 1,4-butanediol, 1,6-hexanediol, 2,5-hexanediol, neopentyl glycol, pinacol, and glycerin. The alicyclic monohydric alcohols include, but are not limited to, cyclopentanol, cyclohexanol, cycloheptanol, cyclooctanol, cyclodecanol, cycloundecanol, cyclododecanol, cyclotetradecanol, cycloicosanol, methylcyclohexanol, cyclohexen-1-ol, cyclocten-1-ol, cyclogeraniol, borneol, menthol, and other aliphatic monohydric alcohols each having a 5- to 30-membered ring. Preferred alicyclic monohydric alcohols are compounds each having a 5- to 30-membered ring, more preferably a 5- to 25-membered ring, and typically a 5- to 20-membered ring (e.g., a 5- to 16-membered ring). The alicyclic polyhydric alcohols include, but are not limited to, 1,2-cyclohexanediol and 1,4-cyclohexanediol. The aromatic alcohols include, but are not limited to, benzyl alcohol, salicyl alcohol, benzhydrol, and phenethyl alcohol.

Of these alcohols, primary or secondary alcohols are preferred, which can be any of aliphatic alcohols, alicyclic alcohols, and aromatic alcohols.

Preferred alcohols include, for example, (1) compounds each having a hydroxyl group at the adjacent position to an unsaturated bond, such as allyl alcohol, benzyl alcohol, benzhydrol, and other unsaturated aliphatic alcohols and aromatic alcohols; (2) alicyclic alcohols such as cyclohexanol, methylcyclohexanol, and other $C_5$–$C_{16}$ cycloalkanols; and (3) alicyclic alcohols each having a tertiary carbon atom (a methine carbon), such as borneol.

Oxidation of these alcohols by oxygen in the presence of the imide compound catalyst yields corresponding aldehydes, ketones, or carboxylic acids. For example, oxidation of alicyclic alcohols yields corresponding alicyclic ketones or polycarboxylic acids depending on the degree of oxidation. For example, oxidation of 2-methylcyclohexanol yields 2-methylcyclohexanone, or further, 2-methyladipic acid.

The aldehydes for use as the substrates include aldehyde derivatives of the hydrocarbons, such as formaldehyde, acetaldehyde, propionaldehyde, butyraldehyde, hexanal, octanal, nonanal, and other $C_1$–$C_{20}$ saturated aliphatic aldehydes; acrolein, geranial (α-citral), citronellal, and other unsaturated aliphatic aldehydes; glyoxal, malonaldehyde, succinaldehyde, glutaraldehyde, adipaldehyde, pimelaldehyde, suberaldehyde, sebacaldehyde, and other aliphatic polyaldehydes, and other aliphatic aldehydes; as well as benzaldehyde, oxybenzaldehyde, cinnamaldehyde, salicylaldehyde, anisaldehyde, 1-naphthylaldehyde, vanillin (vanyllaldehyde), phthalaldehyde, isophthalaldehyde, terephthalaldehyde, and other aromatic aldehydes; formylcyclohexane, and other alicyclic aldehydes; and nicotinaldehyde, furfural, and other heterocyclic aldehydes.

Oxidation of the aldehydes by oxygen in the presence of the imide compound catalyst yields corresponding carboxylic acids. For example, oxidation of adipaldehyde yields adipic acid.

The ketones for use as the substrates include ketone derivatives of the hydrocarbons, such as aliphatic ketones, alicyclic ketones, aromatic ketones, and heterocyclic ketones. The aliphatic ketones include, but are not limited to, acetone, methyl ethyl ketone, diethyl ketone, dipropyl ketone, methyl propyl ketone, methyl butyl ketone, pinacolone, and other $C_2$–$C_{20}$ aliphatic ketones. The alicyclic ketones include, but are not limited to, cyclobutanone, cyclopentanone, cyclohexanone, cyclooctanone, cyclononanone, cyclodecanone, cycloundecanone, cyclododecanone, cyclotetradecanone, cyclooctadecanone, cycloicosanone, 2-methylcyclohexanone, 2-ethylcyclohexanone, 2,6-dimethylcyclohexanone, 4-chlorocyclohexanone, 4-methoxycyclohexanone, cyclohexanediones, cyclopentenones, cyclohexenones, cyclooctenones, cyclodecenones, menthone, camphor, and other alicyclic ketones (cyclic ketones) each having a 4- to 30-membered ring. Preferred alicyclic ketones include compounds each having a 5- to 20-membered ring, of which compounds each having a 5- to 16-membered ring are typically preferred. The aromatic ketones include, but are not limited to, acetophenone, propiophenone, benzophenone, deoxybenzoin, and 1-naphthalenone. The heterocyclic ketones include, but are not limited to, inden-1-one, 1,2,3-indantrione, fluolen-9-one, 4-pyranone, and other heterocyclic ketones.

Oxidation of the ketones by oxygen in the presence of the imide compound catalyst yields corresponding carboxylic acids For example, oxidation of diethyl ketone yields acetic acid and propionic acid, and oxidation of cyclooctanone yields suberic acid.

The amines for use as the substrates are preferably primary or secondary amines, such as methylamine, ethylamine, propylamine, butylamine, dimethylamine, diethylamine, dibutylamine, ethylenediamine, 1,4-butanediamine, hydroxylamine, ethanolamine, and other aliphatic amines; cyclopentylamine, cyclohexylamine, and other alicyclic amines; benzylamine, toluidine, and other aromatic amines. Oxidation of the amines in the presence of the imide compound catalyst yields, for example, corresponding Shiff bases and/or oximes.

The heterocyclic compounds for use as the substrates include (a) non-aromatic heterocyclic compounds or condensed cyclic hydrocarbons each containing a non-aromatic heterocyclic ring, such as pyrane, pyrazoline, piperidine, piperazine, indoline, isoindoline, chromene, xanthene, chroman, and isochroman, and the aforementioned non-aromatic heterocyclic compounds or condensed cyclic hydrocarbons each containing a non-aromatic heterocyclic ring, which further have an alkyl group (e.g., methyl, ethyl, and other alkyl groups each containing from about 1 to about 6 carbon atoms) substituted on the non-aromatic heterocyclic ring; (b) heterocyclic compounds each having an aromatic heterocyclic ring and having a methyl group or methylene group at the adjacent position to the aromatic heterocyclic ring, such as 2-methylfuran, 2,5-dimethylfuran, 2-methylthiophene, 2,5-dimethylthiophene, 2-methylpyridine, 3-methylpyridine, 4-methylpyridine, 2,5-dimethylpyridine, 3-ethylpyridine, 2-methylquinoline, and other heterocyclic compounds each having an alkyl group containing from about 1 to about 6 carbon atoms substituted on an aromatic heterocyclic ring, which aromatic heterocyclic ring has one to three hetero atoms selected from among oxygen atoms, sulfur atoms and nitrogen atoms.

Oxidation of these heterocyclic compounds yields corresponding alcohols, ketones, or carboxylic acids. For example, oxidation of the heterocyclic compounds (a) converts a methylene group at the adjacent position to a hetero atom (e.g., oxygen, sulfur or nitrogen atom) in the non-aromatic heterocyclic ring into a carbonyl group and thereby yields corresponding compounds each having a carbonyl group. Upon oxidation of the heterocyclic compounds (b), the compounds having a methyl group at the adjacent position to an aromatic heterocyclic ring yield corresponding heterocyclic aldehydes or heterocyclic carboxylic acids, and the compounds having a methylene group at the adjacent position to an aromatic heterocyclic ring yield corresponding heterocyclic ketones.

The thiols for use as the substrates include, for example, ethanethiol, and phenylmethanethiol. The sulfides include, for example, diethyl sulfide, methyl propyl sulfide, and diphenyl sulfide. The amides include, for example, formamide and acetamide.

Among these reaction products, preferred compounds are compounds having affinity or eluting capability for organic solvents, and typically for nonpolar organic solvents such as aliphatic hydrocarbons and alicyclic hydrocarbons. Such compounds include, for example, alcohols such as aliphatic alcohols (of which monohydric alcohols are typically preferred), alicyclic monools, and alicyclic diols; aldehydes; ketones; carboxylic acids such as aliphatic monocarboxylic acids, alicyclic monocarboxylic acids, aromatic monocarboxylic acids, aromatic dicarboxylic acids and other aromatic carboxylic acids, and heterocyclic carboxylic acids; epoxy compounds; esters; acid anhydrides; lactones; acetals; ethers; sulfides; amides; lactams; Schiff bases; oximes; nitro compounds; organic sulfur acids; and hydrocarbons, each containing about 5 to about 30, and preferably about 6 to about 30 carbon atoms. Typically preferred reaction products include terpenes each having a carbonyl group, and other conjugated unsaturated carbonyl compounds obtained by oxidation of the unsaturated compounds each having a methylene group (inclusive of a methyl group) at the adjacent position to a carbon-carbon double bond.

The reactions using the imide compound represented by Formula (1) can smoothly proceed under relatively mild conditions. A reaction temperature can be appropriately set depending on the types of the imide compound, reacting agent, and substrate and is, for example, from about 0° C. to about 300° C., preferably from about 30° C. to about 250° C., more preferably from about 40° C. to about 200° C., generally from about 40° C. to about 150° C., and often from about 50° C. to about 100° C. The reaction can be performed at normal pressure or under a pressure (under a load). A reaction time can be appropriately selected within ranges, for example, from about 30 minutes to about 48 hours, preferably from about 1 to about 36 hours, and more preferably from about 2 to about 24 hours depending on the reaction temperature and pressure.

[Altered Catalysts]

After some reactions, a part or all of the imide compound catalyst may alter or convert under some reaction. Examples of such altered catalysts are N-substituted or unsubstituted cyclic imide compounds represented by following Formula (4), cyclic acid anhydrides represented by following Formula (5), and ring-opened derivatives of these compounds:

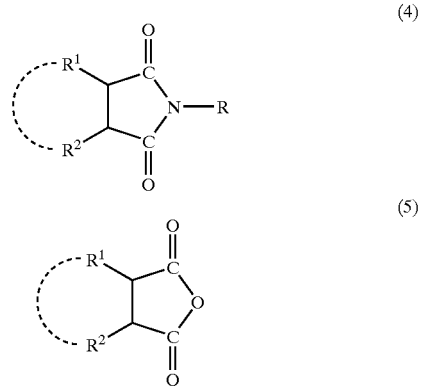

wherein R is a hydrogen atom or a substituted oxy group; and $R^1$ and $R^2$ have the same meanings as defined above.

The substituted oxy group in R in Formula (4) includes, for example, a hydrocarbon-group-substituted oxy group corresponding to a hydrocarbon used as the substrate. For example, oxidation of cyclohexane as the substrate can yield a compound of Formula (4) in which R is a cyclohexyloxy group.

Oxidation of a substrate using N-hydroxyphthalimide as the imide compound catalyst can yield phthalimide (a compound of Formula (4) in which R is a hydrogen atom), a N-substituted oxy-phthalimide corresponding to the substrate (a compound of Formula (4) in which R is a substituted oxy group), phthalic anhydride (a compound of Formula (5)), and ring-opened derivatives of these compounds.

[Separable Two Organic Solvents]

According to the present invention, the reaction product is separated from the imide compound catalyst or altered catalyst by performing an extraction process using two organic solvents separable from each other and dividing the reaction product into on organic solvent layer and the imide compound catalyst or altered catalyst into the other organic solvent layer. At least two organic solvents may be used, and three or more organic solvents can be used as long as they are separable from one another.

Combinations of such two organic solvents separable from each other include a combination of a nonpolar organic solvent and a polar organic solvent. Such nonpolar organic solvents include, for example, aliphatic hydrocarbons and alicyclic hydrocarbons. Such polar organic solvents include, for example, nitriles, alcohols, ketones, esters, acid anhydrides, carboxylic acids, amides, amines, nitrogen-containing heterocyclic compounds, ethers, sulfoxides, sulfones, and nitroalkanes. Each of these solvents can be used alone or as a mixture of two or more solvents of the same or different types.

The aliphatic hydrocarbons include, but are not limited to, pentane, hexane, 2-methylpentane, 2-ethylbutane, 2,2-dimethylbutane, heptane, 2-methylhexane, 2-ethylpentane, octane, 2-ethylhexane, nonane, decane, dodecane, and other aliphatic hydrocarbons each containing about 5 to about 15, and preferably about 5 to about 12 carbon atoms. The alicyclic hydrocarbons include, but are not limited to, cyclopentane, methylcyclopentane, cyclohexane, methylcyclohexane, ethylcyclohexane, dimethylcyclohexanes, cyclooctane, cyclodecane, cyclododecane, and other alicyclic hydrocarbons each containing about 5 to about 15, and preferably about 5 to about 12 carbon atoms.

The nitriles include, for example, acetonitrile. The alcohols include, for example, methanol, ethanol, and ethylene glycol. The ketones include, for example, acetone. The esters include, but are not limited to, ethyl acetate, butyl acetate, and methyl benzoate. The acid anhydrides include, for example, acetic anhydride. The carboxylic acids include, but are not limited to, formic acid and acetic acid. The amides include, for example, N,N-dimethylformamide, N,N-dimethylacetamide, and N-methylpyrrolidone. The amines include, but are not limited to, diethylamine, triethylamine, and ethanolamine. The nitrogen-containing heterocyclic compounds include, for example, pyridine. The ethers include, but are not limited to, tetrahydrofuran, dioxane, and other cyclic ethers, ethylene glycol dimethyl ether, and other chain ethers. The sulfoxides include, for example, dimethyl sulfoxide. The sulfones include, for example, sulfolane. The nitroalkanes include, for example, nitromethane.

The polar organic solvent may contain water. The content of water in the polar organic solvent is, for example, from about 0 to about 1000% by weight, preferably from about 0 to about 100% by weight, more preferably from about 0 to about 25% by weight, and specifically preferably from about 0 to about 5% by weight.

Examples of combinations of such two organic solvents separable from each other are hexane-acetonitrile, cyclohexane-acetonitrile, and other combinations of an aliphatic hydrocarbon or alicyclic hydrocarbon with acetonitrile; hexane-methanol, cyclohexane-methanol, methylcyclohexane-methanol, and other combinations of an aliphatic hydrocarbon or alicyclic hydrocarbon with methanol; octane-acetone, and other combinations of an aliphatic hydrocarbon or alicyclic hydrocarbon with acetone; cyclohexane-acetic anhydride, and other combinations of an aliphatic hydrocarbon or alicyclic hydrocarbon with acetic anhydride.

[Extraction Process]

Extraction can be performed by adding the two organic solvents to a reaction mixture after the reaction or a treated product thereof (e.g., a mixture after a treatment such as concentration, filtration, extraction, distillation, and crystallization), mixing these components, for example, by stirring, and separating them. When an organic solvent for use in extraction is used as a reaction solvent, the reaction solvent can be used as intact in extraction.

The proportions of the two organic solvents can be appropriately selected depending on the types of the reaction product and the imide compound catalyst and/or an altered derivative thereof. Extraction can be performed in any system such as a batch system or a continuous system. Where necessary, extraction may be performed in plural stages. An extraction temperature can be appropriately set in consideration of extraction efficiency and other conditions. To improve the extraction efficiency, extraction may be performed under the application of shearing force and/or under normal pressure or under a pressure (under a load) according to necessity.

The extraction process allows the reaction product to move into a nonpolar organic solvent layer and the imide compound catalyst and/or the altered catalyst to move into a polar organic solvent layer to thereby efficiently separate the reaction product from the catalyst and/or the altered catalyst. An unreacted material (substrate) and a promoter are separated into the nonpolar organic solvent layer or the polar organic solvent layer depending on their properties. The catalyst, reaction product, unreacted material, promoter, and other components, if any, migrated into each layer can be recovered by a conventional separation procedure such as filtration, concentration, distillation, extraction, washing, crystallization, recrystallization, column chromatography, and combinations thereof.

For example, a product of the reaction product with high purity containing very small amounts of the imide compound catalyst and/or the altered catalyst can be obtained by washing the nonpolar organic solvent layer with water, filtrating insoluble matters according to necessity, and concentrating the residue. The resulting product can be further subjected to an appropriate purification means such as distillation and column chromatography to thereby further improve its quality.

The imide compound catalyst or a salt thereof can be recycled or reused in the reaction system by recovering from the polar organic solvent layer and aqueous layers in the washing with water, and further converting the salt, if any, into a free form. The altered catalyst or a salt thereof migrated into the polar organic solvent layer can be converted into the imide compound represented by Formula (1) by subjecting to hydrolysis with an acid or base, ring-closing reaction, ring-opening reaction, or liberation according to necessity, and allowing the resulting substance to react with hydroxylamine or an acid. The regenerated or recovered imide compound can be recycled or reused in the reaction system. In addition, the promoter can be separated and recovered by the extraction process and can be recycled or reused in the reaction system.

INDUSTRIAL APPLICABILITY

The method of the present invention can efficiently separate the reaction product from the imide compound catalyst represented by Formula (1) and/or the altered catalyst in a reaction mixture obtained as a result of a reaction in the presence of the imide compound catalyst by extraction using two organic solvents separable from each other. The method can also simply separate the reaction product from the catalyst under mild conditions without the need of heating at high temperatures. Accordingly, the method can separate the catalyst without decomposition in a separation process, and the recovered catalyst can be reused even when the reaction product is a compound having a high boiling point. The method can also suppress the formation of insoluble matters during extraction. In addition, when the reaction product is, for example, a perfume substance, it can be separated and recovered without deterioration of its quality as a perfume.

EXAMPLES

The present invention will be illustrated in further detail with reference to several examples below, which are not intended to limit the scope of the invention.

Example 1

In a flask 316.1 g (1.1 mol) of valencene with a purity of 71% by weight, 22.28 g (0.14 mol) of N-hydroxyphthalimide, 6.97 g (0.028 mol) of cobalt(II) acetate tetrahydrate, 29.93 g (0.084 mol) of tris(acetylacetonato)cobalt(III), and 3230 g of acetonitrile were placed and were stirred at 40° C. at a pressure of 13 kgf/cm$^2$ (=1.3 MPa) for 2 hours under flow of air at a rate of 150 L (under standard conditions) per hour. The resulting mixture was further treated with 22.84 g (0.14 mol) of N-hydroxyphthalimide with stirring at 40° C. for 2 hours. The reaction mixture was analyzed by gas chromatography and was found that a target compound nootkatone and nootkatol were produced in yields of 53.7% and 1.4%, respectively, with a conversion from valencene of 100%. The reaction mixture was further analyzed by high-performance liquid chromatography and was found to contain 4.4 g of N-hydroxyphthalimide, 0.7 g of phthalimide, and 18.8 g of tris(acetylacetonato)cobalt(III).

The above-obtained reaction mixture was filtrated through a filter paper, and a filtrate was concentrated at 40° C. under reduced pressure (70% concentration). The resulting concentrate was subjected to extraction with four portions of cyclohexane each in an amount as much as two times the weight of the concentrate. Cyclohexane layers were collected, were washed with three portions of pure water each in an equal amount, were filtrated through a filter paper, were subjected to distillation under reduced pressure to remove the solvent and thereby yielded 117 g of nootkatone. The obtained nootkatone was analyzed by gas chromatography and high-performance liquid chromatography and was found that nootkatone was recovered in the purification process with a recovery of 96%, and that N-hydroxyphthalimide, phthalimide, and tris(acetylacetonato)cobalt(III) were removed in the purification process in ratios of 100%, 96%, and 96%, respectively.

Example 2

In a flask 40.87 g (142 mmol) of valencene with a purity of 71% by weight, 4.89 g (30 mmol) of N-hydroxyphthalimide, 0.49 g (2 mmol) of cobalt(II) acetate tetrahydrate, 1.43 g (4 mmol) of tris(acetylacetonato)cobalt(III), 0.58 g (2 mmol) of cobalt nitrate hexahydrate [Co(NO$_3$)$_2$.6H$_2$O], and 360 g of acetonitrile were placed and were stirred at 40° C. at a pressure of 13 kgf/cm$^2$ (=1.3 MPa) for 3 hours under flow of air at a rate of 11.2 L (under standard conditions) per hour. The reaction mixture was analyzed by gas chromatography and was found that a target compound nootkatone and nootkatol were produced in yields of 67.9% and 5.6%, respectively, with a conversion from valencene of 99%. The reaction mixture was further analyzed by high-performance liquid chromatography and was found to contain 0.04 g of N-hydroxyphthalimide, 0.09 g of phthalimide, and 0.59 g of tris(acetylacetonato)cobalt(III).

The above-obtained reaction mixture was filtrated through a filter paper, and a filtrate was concentrated at 40° C. under reduced pressure (70% concentration). The resulting concentrate was subjected to extraction with four portions of cyclohexane each in an amount as much as two times the weight of the concentrate. Cyclohexane layers were collected, were washed with three portions of pure water each in an equal amount, were subjected to distillation under reduced pressure to remove the solvent and thereby yielded 18.6 g of nootkatone. The obtained nootkatone was analyzed by gas chromatography and high-performance liquid chromatography and was found that nootkatone was recovered in the purification process with a recovery of 90%, and that N-hydroxyphthalimide, phthalimide, and tris(acetylacetonato)cobalt(III) were removed in the purification process with ratios of 100%, 95%, and 86%, respectively.

What is claimed is:

1. A method for separating a reaction product from an imide compound catalyst represented by Formula (1) or an altered derivative thereof in a reaction mixture obtained as a result of a reaction in the presence of the imide compound catalyst, the method comprising the step of performing an extraction process using two organic solvents separable from each other, one of said solvents being a nonpolar organic solvent and another of said solvents being a polar organic solvent, to thereby separate the reaction product into a nonpolar organic solvent layer and the imide compound catalyst or an altered derivative thereof into a polar organic solvent layer, respectively:

(1)

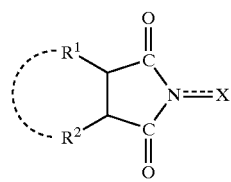

wherein $R^1$ and $R^2$ are the same or different and are each a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, an aromatic ring, or a non-aromatic ring; X is an oxygen atom or a hydroxyl group; and one or two of an N-substituted cyclic imido group indicated in the formula may be further formed on $R^1$, $R^2$, or on the double bond, aromatic ring, or non-aromatic ring formed by $R^1$ and $R^2$.

2. The method according to claim 1, wherein $R^1$ and $R^2$ in the imide compound represented by Formula (1) are combined to form an aromatic or non-aromatic ring having 5 to 12 members.

3. The method according to claim 1, wherein the imide compound represented by Formula (1) is a compound represented by any one of following Formulae (1a), (1b), (1c), (1d), (1e), and (1f):

(1a)

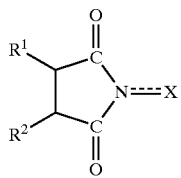

(1b)

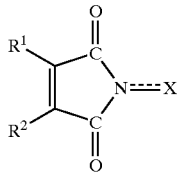

(1c)

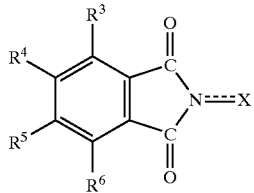

(1d)

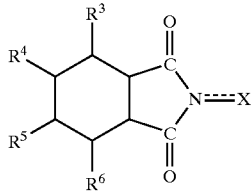

(1e)

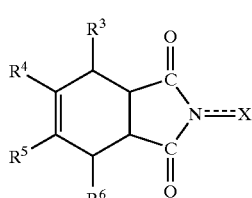

(1f)

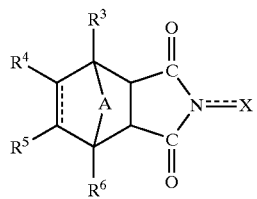

wherein $R^3$, $R^4$, $R^5$, and $R^6$ are the same or different and are each a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom, wherein adjacent groups of $R^3$, $R^4$, $R^5$, and $R^6$ may be combined to form an aromatic or non-aromatic ring; A in Formula (1f) is a methylene group or an oxygen atom; $R^1$, $R^2$ and X have the same meanings as defined above; and wherein one or two of an N-substituted cyclic imido group indicated in Formula (1c) may be further formed on a benzene ring in Formula (1c).

4. The method according to claim 1, wherein the reaction product is at least one selected from the group consisting of alcohols, aldehydes, ketones, carboxylic acids, epoxy compounds, esters, acid anhydrides, lactones, acetals, ethers, sulfides, amides, lactams, Schiff bases, oximes, nitro compounds, organic sulfur acids, and hydrocarbons.

5. The method according to claim 1, wherein the reaction product is a terpene having a carbonyl group.

6. The method according to claim 1, wherein the nonpolar organic solvent is a solvent selected from aliphatic hydrocarbons and alicyclic hydrocarbons, and the polar organic solvent is a solvent selected from the group consisting of nitriles, alcohols, ketones, esters, acid anhydrides, carboxylic acids, amides, amines, nitrogen-containing heterocyclic compounds, ethers, sulfoxides, sulfones, and nitroalkanes.

7. The method according to claim 1, further comprising subjecting the organic solvent layer containing the reaction product to washing with water.

\* \* \* \* \*